United States Patent [19]

Altland et al.

[11] 4,404,390

[45] Sep. 13, 1983

[54] MESOIONIC 1,2,4-TRIAZOLIUM SILVER HALIDE STABILIZER PRECURSORS

[75] Inventors: Henry W. Altland, Rochester; Daniel D. Shiao, Pittsford, both of N.Y.

[73] Assignee: Eastman Kodak Company, Rochester, N.Y.

[21] Appl. No.: 319,567

[22] Filed: Nov. 9, 1981

Related U.S. Application Data

[63] Continuation-in-part of Ser. No. 215,783, Dec. 12, 1980, abandoned.

[51] Int. Cl.³ .......................................... C07D 249/10
[52] U.S. Cl. .................... 548/263; 430/354; 430/419; 430/428; 430/456; 430/560; 430/566; 430/611; 430/613; 430/619; 430/955
[58] Field of Search ......................... 548/263; 548/265

[56] References Cited

U.S. PATENT DOCUMENTS

| | | | |
|---|---|---|---|
| 2,716,062 | 8/1955 | Carroll et al. | 95/7 |
| 2,819,965 | 1/1958 | Murray et al. | 96/109 |
| 3,220,839 | 11/1965 | Herz | 430/566 |
| 3,252,799 | 5/1966 | Götze et al. | 96/109 |
| 3,701,784 | 10/1972 | Seidel | 260/308 |
| 3,740,226 | 6/1973 | Dappen | 430/428 |
| 3,867,395 | 2/1975 | Seidel et al. | 260/308 |
| 3,893,859 | 7/1975 | Burness et al. | 96/61 |
| 3,910,791 | 10/1975 | König et al. | 96/76 |
| 4,003,910 | 1/1977 | Bartels-Keith et al. | 260/308 |
| 4,012,260 | 3/1977 | Dickerson et al. | 96/114.1 |
| 4,259,437 | 3/1981 | Webb | 430/957 |

OTHER PUBLICATIONS

Becker et al, J. Prakt. Chem., vol. 315, pp. 1131–1138 (1973).
Lazaris et al, Journal of Organic Chemistry of the USSR, vol. 8, pp. 1569–1572 (1972).
Research Disclosure, Dec. 1978, Item No. 17643.
Research Disclosure, Jun. 1978, Item No. 17029.
Research Disclosure, Jan. 1979, Item No. 17710.
J. C. S. Perkin I, pp. 633–638, 1974, by W. David Ollis et al.
Potts et al, Journal of Organic Chemistry, 37 (7), pp. 2245–2252 (1967).
Potts et al, Chemical Abstracts, 63:2966b (1965).
Duffin et al, Journal of Chemical Society, 1959, pp. 3700–3808.

*Primary Examiner*—Alton D. Rollins
*Attorney, Agent, or Firm*—Richard E. Knapp

[57] ABSTRACT

Mesoionic 1,2,4-triazolium-3-thiolate silver halide stabilizer precursors are novel compounds useful in a heat developable and heat stabilizable photographic silver halide materials and processes. After imagewise exposure of the photographic material, a developed and stabilized silver image is produced by heating the element. Mesoionic stabilizer precursors are also useful in photographic silver halide processing compositions.

7 Claims, No Drawings

MESOIONIC 1,2,4-TRIAZOLIUM SILVER HALIDE STABILIZER PRECURSORS

FIELD OF THE INVENTION

This invention relates to mesoionic 1,2,4-triazolium-3-thiolate silver halide stabilizer precursors and the use of such precursors in heat developable and heat stabilizable photographic silver halide materials and processes. It also relates to use of such stabilizer precursors in photographic silver halide processing compositions.

DESCRIPTION OF THE STATE OF THE ART

Mesoionic sulfur-containing tetrazole compounds have been described in the photographic art as photographic additives in, for instance, U.S. Pat. No. 4,003,910. These compounds are not described as useful in a heat developable and heat stabilizable photographic material and process.

The use of stabilizer precursors in heat developable and heat stabilizable photographic materials and processes is known. Examples of known stabilizer precursors are described in, for instance, U.S. Pat. No. 4,012,260. An example of a heterocyclic stabilizer precursor is 2-amino-2-thiazolinium trichloroacetate.

A related heat developable and heat stabilizable photographic silver halide material comprising photographic silver halide, a photographic silver halide developing agent, an activating concentration of a thermal base releasing compound, and a stabilizing concentration of a mesoionic 1,2,4-triazolium-3-thiolate silver halide stabilizer is described in copending U.S. application Ser. no. 215,786 of H. W. Altland, E. L. Dedio and G. J. McSweeney, filed Dec. 12, 1980, entitled "Mesoionic Silver Halide Stabilizer in a Heat Developable and Heat Stabilizable Photographic Silver Halide Material and Process", now abandoned. A problem exists with such materials containing a stabilizer in that the stabilizer can cause undesired sensitometric changes in the photographic silver halide prior to exposure and processing. No suitable answer to this problem is found in the copending application or in the above patents.

A continuing need has existed for stabilizers that provide water-soluble light-insensitive silver (I) complexes upon exposure and heating of a heat developable and heat stabilizable photographic silver halide material. Such water-soluble light-insensitive silver (I) complexes help provide light stability to a developed image in a processed photographic silver halide element.

The term "material" as used herein, such as in "photographic silver halide material," refers to photographic elements and photographic compositions. For instance, the term "heat developable and heat stabilizable photographic silver halide material" refers to photographic elements and photographic compositions that are heat developable and heat stabilizable.

SUMMARY OF THE INVENTION

The heterocyclic sulfur-containing silver halide stabilizer precursor, according to the invention, comprises a novel 1,2,4-triazolium-3-thiolate silver halide stabilizer precursor in which the sulfur atom is blocked by an appropriate blocking group which is released upon processing at processing temperature. The silver halide stabilizer precursor provides, upon heating and after development of an exposed photographic silver halide material, a stabilized silver image.

According to the invention, a developed and stabilized silver image is provided in a heat developable and heat stabilizable photographic silver halide material. This material, according to the invention, comprises, in reactive association, in binder:

(a) photographic silver halide, preferably as a photographic silver halide gelatino emulsion;
(b) a photographic silver halide developing agent;
(c) an activating concentration of a thermal base releasing compound; and
(d) a stabilizing concentration of a heterocyclic sulfur-containing silver halide stabilizer precursor.

DETAILED DESCRIPTION OF THE INVENTION

Many blocked mesoionic 1,2,4-triazolium-3-thiolates are useful silver halide stabilizer precursors according to the invention. Combinations of such stabilizer precursors are also useful. Selection of an optimum stabilizer precursor, or combination of stabilizer precursors, will depend upon such factors as the desired image stability, processing conditions, the particular silver halide and the photographic material, the particular silver halide developing agent, and other addenda in the photographic material. Examples of particular useful mesoionic 1,2,4-triazolium-3-thiolate stabilizer precursors are represented by the formula:

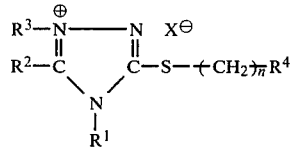

wherein:

$R^1$ is alkyl containing 1 to 18 carbon atoms, such as methyl, methoxymethyl, 2-methoxyethyl, 3-methoxypropyl, ethyl, propyl, butyl, decyl, benzyl, 2-phenethyl and octadecyl, amino, including

alkenyl containing 3 to 18 carbon atoms, such as allyl, 2-butenyl and crotonyl, cycloalkyl containing 3 to 12 carbon atoms such as cyclohexyl and cycloheptyl, aryl containing 6 to 20 carbon atoms, such as phenyl, 4-tolyl and α-naphthyl;

$R^2$ is alkyl containing 1 to 9 carbon atoms, such as methyl, ethyl, propyl and pentyl, aryl containing 6 to 12 carbon atoms such as phenyl, 4-tolyl, or α-naphthyl;

$R^3$ is alkyl containing 1 to 18 carbon atoms, such as methyl, ethyl, propyl, pentyl and octadecyl; aryl containing 6 to 20 carbon atoms, such as phenyl and α-naphthyl; or cycloalkyl containing 3 to 12 carbon atoms, such as cyclohexyl and cyclopentyl;

—$(CH_2)_n$—$R^4$ is a heat releasable blocking group on the sulfur atom; and $R^4$ is alkyl containing 1 to 18 carbon atoms, such as methyl, ethyl, propyl, decyl and octadecyl, aryl containing 6 to 20 carbon atoms, such as phenyl and α-naphthyl, carboxyaryl containing 7 to 13 carbon atoms, including carboxyphenyl, and carboxynaphthyl; cyano (CN) or amido ($CONH_2$);

$R^5$ and $R^6$ are individually hydrogen, alkyl containing 1 to 18 carbon atoms, such as methyl, ethyl, propyl and decyl, or aryl containing 6 to 20 carbon atoms, such as phenyl, 4-tolyl and α-naphthyl, provided that when one of $R^5$ and $R^6$ is alkyl then both $R^5$ and $R^6$ are alkyl;

n is 1 or 2; and

X is an acid anion, such as a halide anion, a nitrate anion, or $BF_4^\ominus$.

The term "alkyl" as used herein means unsubstituted alkyl and alkyl substituted by means of a group which does not adversely affect the desired sensitometric properties of the photographic silver halide and does not adversely affect the desired stabilizing properties of the stabilizer resulting from the stabilizer precursor according to the invention. Examples of suitable substituents on the alkyl include alkoxy, such as methoxy; phenyl; 2-carboxyphenyl and cyano. The term "alkyl" includes alkoxyalkyl, such as alkoxyalkyl containing 2 to 12 carbon atoms, and aralkyl, such as benzyl and 2-phenethyl.

An especially useful 1,2,4-triazolium-3-thiolate precursor is 1,4,5-trimethyl-3-(2-carboxybenzylthio)-1,2,4-triazolium nitrate represented by the formula (Compound A):

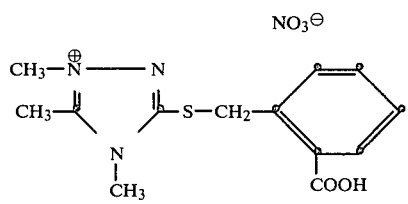

Examples of other useful 1,2,4-triazolium-3-thiolate stabilizer precursors include:

1,4,5-Trimethyl-3-(carboxamidomethylthio)-1,2,4-triazolium trifluoroacetate (Compound B) represented by the formula:

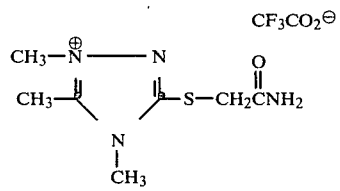

1,5-Dimethyl-3-(carboxamidomethylthio)-4-amino-1,2,4-triazolium trifluoroacetate (Compound C) represented by the formula:

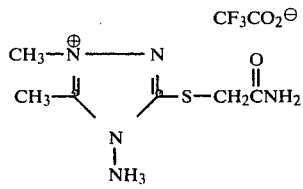

1,5-Dimethyl-3-(cyanomethylthio)-4-amino-1,2,4-triazolium tetrafluoroborate (Compound D) represented by the formula:

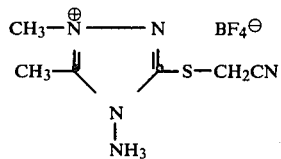

1,4,5-Trimethyl-3-(carboxamidomethylthio)-1,2,4-triazolium dichloroacetate (Compound E) represented by the formula:

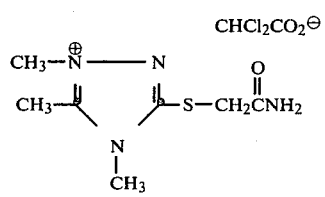

1,5-Dimethyl-3-(carboxamidomethylthio)-4-(2-methoxyethyl)-1,2,4-triazolium nitrate (Compound F) represented by the formula:

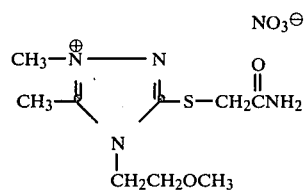

1,4,5-Trimethyl-3-(cyanomethylthio)-1,2,4-triazolium tetrafluoroborate (Compound G) represented by the formula:

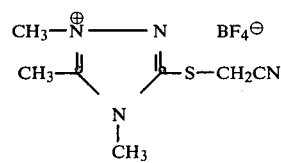

1,4,5-Trimethyl-3-(4-carboxybenzylthio)-1,2,4-triazolium nitrate (Compound H) represented by the formula:

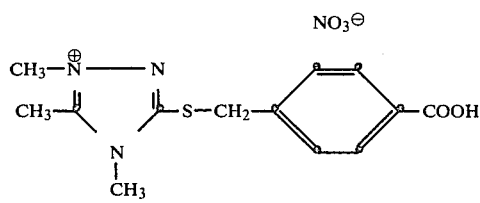

1,4,5-Trimethyl-3-(2-carboxy-6-nitrobenzylthio)-1,2,4-triazolium nitrate (Compound I) represented by the formula:

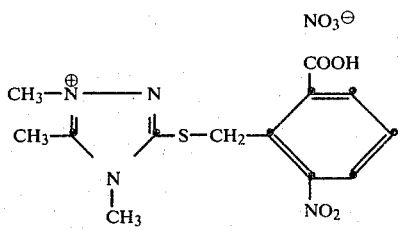

1,4,5-Trimethyl-3-(2-carboxy-3-nitrobenzylthio)-1,2,4-triazolium nitrate (Compound J) represented by the formula:

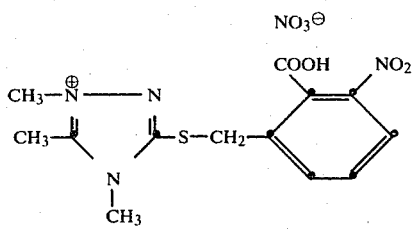

The mesoionic 1,2,4-triazolium-3-thiolate stabilizer precursors are prepared by methods known in the organic chemical synthesis art. The parent compounds from which the stabilizer precursors are prepared are also prepared by methods known in the chemical art. The preparation of the parent compound 1,4,5-trimethyl-1,2,4-triazolium-3-thiolate illustrates preparation of a parent compound:

Acetic anhydride (10.2 g, 0.1 mole) was slowly added to a stirred distilled water (11 g) solution of methyl hydrazine (4.6 g, 0.1 mole) at ice bath temperature. The resulting solution was stirred at room temperature for one hour and the water was removed under reduced pressure. The residual oily acethydrazide was suspended in ethyl ether and to this stirred mixture at room temperature was slowly added an ether (25 ml) solution of methyl isothiocyanate (7.3 g, 0.1 mole). The resulting stirred solution was kept at room temperature for thirty minutes and then the solvent was removed under reduced pressure. The residual colorless solid was triturated with ethyl ether to provide 4.9 grams (30 percent) of the desired thiosemicarbazide (a white powder) having a melting point of 180° to 181° C. The thiosemicarbazide (5.0 g, 0.03 mole) was refluxed in methanol (25 ml) solution for 21 hours. During this reflux period, the thiosemicarbazide completely dissolved in the refluxing methanol and a colorless solid then separated. The solid had a melting point of 258° to 259° C.

Crude acethydrazide (CH₃N(COCH₃)NH₂), prepared from acetic anhydride (10.2 g, 0.1 mole) and methyl hydrazine (4.6 g, 0.1 mole) as described above was dissolved in ethyl ether (25 ml) and to the resulting stirred translucent solution at room temperature was slowly added an ether (25 ml) solution of 2-methoxyethyl isothiocyanate (11.7 g, 0.1 mole). After keeping the stirred solution at ambient temperature for one hour, the ether was removed under reduced pressure. More ethyl ether was added to the residual pale yellow syrup, and the resulting colorless solid was stirred at ambient temperature for 18 hours. This provided a product having a melting point of 122° to 123° C. The thiosemicarbazide (2.4 g, 0.012 mole) was heated to its melting point (above 123° C.) for 5 hours. After cooling to ambient temperature, the crystalline residue was crystallized from ethyl acetate-ethanol to provide 1.3 grams (59 percent) of pale yellow plates having a melting point of 125° to 126° C. The structure of the desired product was confirmed by mass spectral analysis and nuclear magnetic resonance.

An illustration of a different method of preparation of a parent 1,2,4-triazolium-3-thiolate is the preparation of 1,5-dimethyl-4-(2-methoxyethyl)-1,2,4-triazolium-3-thiolate:

A stirred dichloromethane (40 ml) mixture of 2-methoxyethylisocyanide dichloride (1.9 g, 0.012 mole) and CH₃—CS—N(CH₃)NH₂ (1.3 g, 0.012 mole) was refluxed for two hours. The solvent was then removed under reduced pressure and the residual orange semi-solid was dissolved in 50 ml of methanol. One-half of this solution was evaporated to dryness and the residue was then dissolved in methylene chloride (50 ml). Ammonia gas was bubbled through this stirred solution at ambient temperature for about five minutes. The resulting precipitate (presumably ammonium chloride) was collected and the filtrate was evaporated to dryness to yield a reddish-brown semi-solid. A stirred ethanol (50 ml) solution of this solid was refluxed for 18 hours. Solvent was removed under reduced pressure to give a slowly crystallizing orange oil. An ethyl acetate solution of this material was treated with decolorizing carbon and was eluted through a suitable filter material (Celite). The ethyl acetate eluate was concentrated to about 25 ml and the desired colorless plates separated. The desired compound was formed having a melting point of 123° to 125° C. The desired product was identified by nuclear magnetic resonance and mass spectral analysis.

The preparation of 1,4,5-trimethyl-3-(2-carboxybenzylthio)-1,2,4-triazolium nitrate illustrates preparation of a 1,2,4-triazolium-3-thiolate stabilizer precursor according to the invention:

A stirred methanol (75 ml) solution of 1,4,5-trimethyl-1,2,4-triazolium-3-thiolate (5.7 g, 0.04 mole) and α-bromo-2-toluic acid (8.6 g, 0.04 mole) was refluxed for one hour. The solvent was removed under reduced pressure and the residual syrup was dissolved in about 20 ml of methanol. Ethyl ether was added to this stirred solution until a permanent cloudiness has resulted. This mixture was chilled for 18 hours. At the end of this time, an oil, out of which a colorless solid was forming, had separated. This mixture was rapidly stirred at ambient temperature until the formation of a colorless solid appeared complete. The resulting snow-white solid was collected, washed with ethyl ether and dried. This produced the desired product which had a melting point of 175° to 176° C. and was identified by elemental analysis, as well as by nuclear magnetic resonance and other analytical techniques.

Propylene oxide (1.8 g, 0.03 mole) in methanol (25 ml) was added slowly to a stirred methanol (25 ml) mixture of 1,4,5-trimethyl-3-(2-carboxybenzylthio)-1,2,4-triazolium bromide (2.0 g, 0.006 mole) and 70.7 percent nitric acid (0.9 g, 0.01 mole) at 2° C. The resulting stirred solution was kept at ambient temperature for 18 hours. Solvents were removed under reduced pressure and the residual clear colorless oil was crystallized with methanol-ethyl ether. The resulting desired product had a melting point of 139° to 140° C. and was identified by nuclear magnetic resonance, mass spectral analysis and by other analytical techniques.

The desired products are purified by procedures known in the chemical art, such as by recrystallization.

One embodiment of the invention is a heat developable and heat stabilizable photographic silver halide element comprising a support having thereon, in reactive association, binder:
(a) photographic silver halide, preferably as a photographic silver halide gelatino emulsion;
(b) a photographic silver halide developing agent;
(c) an activating concentration of a thermal base releasing compound; and
(d) a stabilizing concentration of a silver halide stabilizer precursor comprising a 1,2,4-triazolium-3-thiolate stabilizer precursor according to the invention.

The photographic material according to the invention comprises photographic silver halide. Useful photographic silver halides include, for example, silver chloride, silver bromide, silver bromoiodide, silver chlorobromoiodide and mixtures thereof. The grain size of the silver halide ranges from coarse-grain to fine-grain. The photographic silver halide is prepared by procedures known in the photographic art, as described in, for example, *Research Disclosure,* December 1978, Item No. 17643, and *Research Disclosure,* June 1978, Item No. 17029. The photographic materials according to the invention, if desired, also contain addenda which do not adversely affect the desired properties of the materials, such as antifoggants, tone modifiers, chemical sensitizers, hardeners, matting agents, brighteners, absorbing and filter dyes, development modifiers, spectral sensitizers and coating aids, as described in these *Research Disclosure* publications.

Many antifoggants are useful in a photographic material according to the invention. Useful antifoggants are selected from those described in, for example, *Research Disclosure,* December 1978, Item No. 17643. Tetraazaindene antifoggants are especially useful. Such tetraazaindene antifoggants are described in, for example, U.S. Pat. No. 2,716,062.

The heat developable and heat stabilizable photographic materials according to the invention contain binders and vehicles, alone or in combination. Suitable vehicle materials include both naturally-occurring substances such as protein, for example, gelatin, gelatin derivatives, cellulose derivatives, polysaccharides such as dextrin, gum arabic and the like; and synthetic polymeric materials such as water-soluble polyvinyl compounds like poly(vinylpyrrolidone), acrylamide polymers and the like. The photographic layers and other layers of the elements of the invention such as overcoat layers, interlayers and subbing layers can also contain, alone or in combination with the described vehicles, other synthetic polymeric vehicle compounds, such as dispersed vinyl compounds, such as in latex form, and particularly those which increase the dimensional stability of the photographic materials. Useful binders are also described in the above *Research Disclosure* publications. Selection of an optimum binder depends upon such factors as the processing conditions, the particular components of the photographic material and the desired image.

Many supports are useful for a photographic element according to the invention. Typical supports include those which are resistant to adverse changes in structure and do not adversely affect the sensitometric properties of the described photographic materials at the processing temperatures employed. Typical supports include cellulose ester film, poly(vinyl acetal) film, poly(ethylene terephthalate) film, polycarbonate film and related films and resinous materials, as well as glass, paper, metal and the like. Typically, a flexible support is employed, especially a paper support.

The heat developable and heat stabilizable layer and other layers of a photographic element according to the invention are coated by means of coating procedures known in the photographic art. Such procedures are described in, for example, the above *Research Disclosure* publications.

The stabilizer precursor according to the invention is in a location in the photographic material according to the invention which enables the stabilizer precursor upon processing to form a stabilizer moiety and react with the silver halide in the unexposed areas upon processing to form a stable silver (I) salt. The stabilizer precursor is useful in one or more layers of a photographic element according to the invention. The stabilizer precursor is preferably in the layer containing the silver halide. Alternatively, the stabilizer precursor is in an overcoat layer or in a layer between the support and the layer containing silver halide. It is important that the stabilizer precursor be in a location which enables the desired interaction between the moiety produced upon heating the stabilizer precursor and the silver halide in the photographic material according to the invention after desired development of the exposed silver halide. The term "in reactive association" herein means that the stabilizer precursor is in such a location enabling such desired interaction.

Many silver halide developing agents are useful in a photographic silver halide material and process according to the invention. Combinations of silver halide developing agents are useful. Useful silver halide developing agents include, for instance, those described in *Research Disclosure,* June 1978, Item No. 17029. Examples of useful silver halide developing agents are ascorbic acid developing agents, such as ascorbic acid, ascorbic acid ketals, and ascorbic acid derivatives; reductone developing agents, such as anhydrodihydropiperidinohexose reductone, 3-pyrazolidone developing agents, such as 4-methyl-4-hydroxymethyl-1-phenyl-3-pyrazolidone and 1-phenyl-3-pyrazolidone; and phenolic developing agents, such as polyhydroxybenzene developing agents, including hydroquinone. A preferred silver halide developing agent is ascorbic acid and 4-hydroxymethyl-4-methyl-1-phenyl-3-pyrazolidone.

Many thermal base releasing compounds are useful in a heat developable and heat stabilizable photographic material according to the invention. The term "thermal base releasing compound" herein means a compound which releases a base, preferably an organic base, when heated in a photographic material according to the invention to processing temperature. The base released activates development of the exposed photographic silver halide in the photographic material according to the invention at processing temperature. The activating concentration of the base release agent herein means that the concentration of base release agent is sufficient in the photographic material to release a sufficient amount of base upon processing to activate development. The base released also helps stabilization by aiding in deblocking the stabilizer precursor according to the invention. Examples of useful thermal base releasing compounds are described in *Research Disclosure,* June 1978, Item No. 17029 and include guanidinium trichloroacetate, 1,1-dimethyl-1-(2-hydroxypropyl)-amine adipimide, 1-(β-aminoethyl)-2-imidazolidone trichloroacetate, zinc oxide and urea.

The optimum concentration of each of (a) photographic silver halide, (b) photographic silver halide developing agent, (c) thermal base release agent, and (d) stabilizer precursor according to the invention will depend upon such factors as the desired image, processing conditions and particular components of the heat developable and heat stabilizable photographic material. In a photographic element according to the invention, useful concentrations are within the following ranges:

(a) photographic silver halide: $2.5 \times 10^{-3}$ to $1.0 \times 10^{-1}$ moles, preferably $1.0 \times 10^{-2}$ to $3.0 \times 10^{-2}$ moles;

(b) photographic silver halide developing agent: $2.5 \times 10^{-3}$ to $1.0 \times 10^{-1}$ moles, preferably $1.0 \times 10^{-2}$ to $3.0 \times 10^{-2}$ moles;

(c) thermal base releasing agent: $1.25 \times 10^{-3}$ to $5.0 \times 10^{-2}$ moles, preferably $5.0 \times 10^{-3}$ to $1.5 \times 10^{-2}$ moles; and (d) stabilizer precursor: $2.5 \times 10^{-3}$ to $1.0 \times 10^{-1}$ moles, preferably $1.0 \times 10^{-2}$ to $3.0 \times 10^{-2}$ moles;

per square meter of support.

An especially useful heat developable and heat stabilizable photographic material according to the invention comprises, in reactive association, in a gelatino binder:

(a) photographic silver halide gelatino emulsion;

(b) a photographic silver halide developing agent, such as ascorbic acid, 1-phenyl-3-pyrazolidone or 4-hydroxymethyl-4-methyl-1-phenyl-3-pyrazolidone;

(c) an activating concentration of a thermal base releasing compound consisting essentially of an ethylenebis(sulfonylacetic acid) compound; and (d) a stabilizing concentration of a 1,2,4-triazolium-3-thiolate stabilizer precursor consisting essentially of mesoionic 1,4,5-trimethyl-3-(2-carboxybenzyl-thio)-1,2,4-triazolium nitrate.

The stabilizer precursors according to the invention are useful in photographic silver halide processing compositions that enable use of the silver halide stabilizing properties of the stabilizer precursors according to the invention. Such photographic silver halide processing compositions include silver halide developers, stabilizing compositions, fixing compositions, hardeners and other processing compositions that enable the stabilizer precursor according to the invention to form a moiety which produces a silver (I) complex without adversely affecting desired properties of the processing composition and the photographic silver halide material. An example of a silver halide processing composition comprises a silver halide developing agent, a thermal base release agent, and a stabilizing concentration of a stabilizer precursor according to the invention, such as mesoionic 1,4,5-trimethyl-3-(2-carboxybenzylthio)-1,2,4-triazolium nitrate. The processing composition generally comprises a solvent or binder.

Because the stabilizer precursor according to the invention provides a moiety which can produce a stable silver (I) complex, no additional silver halide stabilizer is necessary in a photographic material according to the invention. However, added silver halide stabilizers and stabilizer precursors are useful in the photographic silver halide according to the invention, if desired. Stabilizers and stabilizer precursors that are useful in a photographic silver halide material according to the invention are described in *Research Disclosure*, June 1978, Item No. 17029. An example of a combination of stabilizer precursors is the combination of 1,4,5-trimethyl-3-(2-carboxybenzylthio)-1,2,4-triazolium nitrate with 2-amino-2-thiazolinium trichloroacetate.

Exposure of a photographic silver halide material according to the invention is by means of forms of energy to which the silver halide is sensitive. The photographic silver halide material is generally imagewise exposed to light. Alternatively, other forms of energy are useful, such as electron beams, X-rays, gamma rays, alpha particles and other nuclear particles. Lasers are also useful. Imagewise exposure of the photographic silver halide material is generally sufficient in time and intensity to provide a developable latent image in the photographic silver halide material.

After exposure of a photographic silver halide material according to the invention, an image is developed and stabilized by heating the material to a processing temperature within the range of about 100° C. to about 180° C., such as about 130° C. to about 140° C., until the image is developed and stabilized. An image is generally developed and stabilized by heating the photographic silver halide material to a processing temperature within the range of about 100° C. to about 180° C. for about one to about 60 seconds, such as about 10 to about 30 seconds.

Processing is carried out under ambient conditions of pressure and humidity. Normal atmospheric conditions of pressure and humidity are preferred for processing.

Various means are useful for heating the exposed photographic silver halide material according to the invention. The photographic silver halide material containing the developable image is generally brought into contact with a simple hot plate, iron, rollers, dielectric heating means, heated drum or microwave heating means.

The following examples are included for a further understanding of the invention.

EXAMPLE 1

Use of a Stabilizer Precursor

The following composition was coated on a gelatin subbed poly(ethylene terephthalate) film support and dried at room temperature (about 20° C.):

| Component | Coverage |
| --- | --- |
| photographic gelatin | 32.4 mg/dm$^2$ |
| surfactant (Surfactant 10G, a para-isononylphenoxypolyglycidol, a trademark of and available from the Olin Corporation, U.S.A.) | 2.2 mg/dm$^2$ |
| methylsuccinic acid | 14.1 mg/dm$^2$ |
| silver bromoiodide gelatino emulsion (0.14 micron grain, unsensitized, 2.5 mole percent iodide) | 10.8 mg/dm$^2$ |
| 1,4,5-trimethyl-3-(2-carboxy-benzylthio)-1,2,4-triazolium nitrate (stabilizer precursor) | 44.3 mg/dm$^2$ |

The melt pH of the composition was adjusted to 4.5 by means of 1 N-potassium hydroxide. The resulting photographic element was heated at 140° C. for 15 seconds. The heated element was light stable and transparent (specular density of 0.25).

A similar photographic element was used to determine silver halide dissolution (initial) rates, identified as $r_{id}$, at 120° C. and 38° C. The ratio $R_d$ of the $r_{id}$'s at these two temperatures was a measure of the activation energy for silver halide dissolution according to the following equation:

$$R_d = \frac{r_{id} \text{ at } 120° \text{ C.}}{r_{id} \text{ at } 38° \text{ C.}}$$

From the incubation stability point of view, a compound was considered to be useful as a stabilizer precursor if its $R_d$ value was larger than $10^3$. The $R_d$ value for the stabilizer precursor of this example was 2.0 times $10^4$.

EXAMPLE 2

The following composition was prepared and coating on a poly(ethylene terephthalate) film support at a wet coating thickness of 0.01 centimeter:

| Component | Coverage (Amount per dm²) |
|---|---|
| photographic gelatin | 43.2 mg |
| silver chloride gelatino emulsion (0.24 micron grain size, unsensitized) | 0.119 mmole |
| ascorbic acid (silver halide developing agent) | 0.076 mmole |
| maleic acid (buffer) | 0.150 mmole |
| [H₂N—(CH₂)₃—NHCO—NH—CH₂]₂—CH₂ (modifier) | 0.032 mmole |
| 4-hydroxy-6-methyl-1,3,3a,7-tetraazaindene (antifoggant) | 1.1 mg |
| 1,4,5-trimethyl-3-(2-carboxybenzylthio)-1,2,4-triazolium nitrate (stabilizer precursor) | 0.161 mmole |
| surfactant (Surfactant 10G) | 1.1 mg |

The melt pH for the described composition was adjusted to 4.5 by means of 1 N-potassium hydroxide. The resulting photographic element was permitted to dry and then was overcoated with 50 mg per square foot of polymethyl methacrylate from a dichloromethane solution. This produced a heat developable and heat stabilizable photographic material according to the invention.

The photographic element was sensitometrically exposed to white light in a commercial sensitometer and then heated for 15 seconds at 140° C. A developed and stabilized image was produced having a maximum density (diffused) of 1.5 and a minimum density of 0.6.

The following compounds in the following Tables A and B were prepared by a procedure similar to that described above:

TABLE A

[Reaction scheme showing triazolium compound + R⁴I with heat/CH₃OH producing substituted product with I⁻ counterion]

| Example | R¹ | R⁴ |
|---|---|---|
| 3 | CH₃ | CNH₂ (C=O) |
| 4 | NH₂ | CNH₂ (C=O) |
| 5 | CH₂CH₂OCH₃ | CNH₂ (C=O) |
| 6 | CH₃ | CN |
| 7 | NH₂ | CN |

TABLE B

[Reaction scheme showing triazolium intermediate with I⁻ + epoxide (CH₃—CH—CH₂ with O) + HX in CH₃OH producing product with X⁻ counterion]

| Example | R¹ | R⁴ | X |
|---|---|---|---|
| 8 | CH₃ | CNH₂ (C=O) | CF₃CO₂ |
| 9 | NH₂ | CNH₂ (C=O) | CF₃CO₂ |
| 10 | CH₂CH₂OCH₃ | CNH₂ (C=O) | NO₃ |
| 11 | CH₃ | CN | BF₄ |
| 12 | CH₃ | CNH₂ (C=O) | CHCl₂CO₂ |
| 13 | NH₂ | CN | BF₄ |

The products in Tables A and B were identified by elemental analysis and other known analytical procedures.

The compounds in the following Table C can be used to obtain a stabilized image similar to that in Example 2:

TABLE C

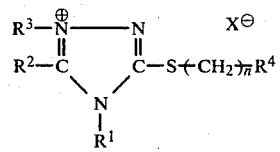

| Example | n | R¹ | R² | R³ | X | R⁴ |
|---|---|---|---|---|---|---|
| 3 | 1 | CH₂CH₂OCH₃ | phenyl | CH₃ | NO₃ | phenyl-COOH |
| 4 | 1 | CH₃ | CH₃ | i-propyl | NO₃ | phenyl-COOH |
| 5 | 1 | i-propyl | CH₃ | CH₃ | NO₃ | phenyl-COOH |
| 6 | 1 | CH₃ | CH₃ | dodecyl | NO₃ | phenyl-COOH |
| 7 | 1 | phenyl | phenyl | CH₃ | NO₃ | phenyl-COOH |
| 8 | 1 | CH₃ | C₂H₅ | 4-tolyl | NO₃ | $\overset{O}{\underset{\|}{C}}NH_2$ |
| 9 | 1 | phenyl | CH₃ | CH₃ | NO₃ | $\overset{O}{\underset{\|}{C}}NH_2$ |
| 10 | 1 | pentyl | CH₃ | phenyl | BF₄ | phenyl-COOH |
| 11 | 1 | C₂H₅ | CH₃ | CH₃ | NO₃ | phenyl-COOH |
| 12 | 1 | 4-methoxyphenyl | CH₃ | CH₃ | NO₃ | phenyl-COOH |

TABLE C-continued
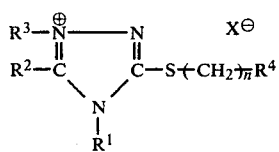
| Example | n | R¹ | R² | R³ | X | R⁴ |
|---|---|---|---|---|---|---|
| 13 | 1 | CH₂CH(OCH₃)₂ | CH₃ | CH₃ | NO₃ | —C₆H₄—COOH |
| 14 | 1 | CH₃ | i-propyl | CH₃ | NO₃ | —C₆H₄—COOH |
| 15 | 1 | C₁₈H₃₇ | CH₃ | CH₃ | NO₃ | —C₆H₄—COOH |
| 16 | 1 | CH₃ | C₅H₁₁ | CH₃ | CF₃CO₂ | —C₆H₄—COOH |
| 17 | 1 | NH₂ | CH₃ | CH₃ | NO₃ | —C₆H₄—COOH |
| 18 | 1 | CH₂CH=CH₂ | CH₃ | CH₃ | NO₃ | —C₆H₄—COOH |
| 19 | 1 | CH₃ | CH₃ | cyclohexyl | NO₃ | —C₆H₄—COOH |
| 20 | 1 | NHC₆H₅ | C₉H₁₉ | CH₃ | NO₃ | —C₆H₄—COOH |
| 21 | 1 | N(C₂H₅)₂ | CH₃ | CH₃ | NO₃ | —C₆H₄—COOH |

TABLE C-continued $$\begin{array}{c} R^3-\overset{\oplus}{N}\!\!-\!\!\!-\!\!\!-\!\!N \quad X^{\ominus} \\ R^2-C \quad\quad C-S\!-\!(CH_2)_n\!-\!R^4 \\ \diagdown N \diagup \\ | \\ R^1 \end{array}$$

| Example | n | $R^1$ | $R^2$ | $R^3$ | X | $R^4$ |
|---|---|---|---|---|---|---|
| 22 | 1 | $N(i\text{-}C_3H_7)_2$ | $CH_3$ | $CH_3$ | $NO_3$ | (2-carboxyphenyl) |

COMPARATIVE EXAMPLE

The following compounds were prepared:

$$\begin{array}{c} CH_3-\overset{\oplus}{N}\!\!-\!\!\!-\!\!\!-\!\!N \quad X^{\ominus} \\ R^6-C \quad\quad C-S-R^7 \\ \diagdown N \diagup \\ | \\ R^5 \end{array}$$

wherein:
$R^5$ is $CH_3-$, $C_6H_5-$ or $NH_2$;
$R^6$ is $CH_3-$ or $C_6H_5-$;
$R^7$ is $CH_3-$ or $4-NO_2C_6H_5CH_2-$;
$X^{\ominus}$ is $NO_3^{\ominus}$, $BF_4^{\ominus}$ or $CF_3CO_2^{\ominus}$.

The compound in each instance was heated at 180° C. for ten seconds. In each case, no significant concentration of the parent 1,2,4-triazolium-3-thiolate was observed to be formed.

The invention has been described in detail with particular reference to preferred embodiments thereof, but it will be understood that variations and modifications can be effected within the spirit and scope of the invention.

What is claimed is:

1. A mesoionic 1,2,4-triazolium-3-thiolate precursor represented by the formula:

$$\begin{array}{c} R^3-\overset{\oplus}{N}\!\!-\!\!\!-\!\!\!-\!\!N \quad X^{\ominus} \\ R^2-C \quad\quad C-S-(CH_2)_n\!-\!R^4 \\ \diagdown N \diagup \\ | \\ R^1 \end{array}$$

wherein:
$R^1$ is alkyl containing 1 to 18 carbon atoms, $$\begin{array}{c} \quad\quad R^6 \\ \quad\diagup \\ -N \\ \quad\diagdown \\ \quad\quad R^5 \end{array}$$, alkenyl containing 3 to 18 carbon atoms, cycloalkyl containing 3 to 12 carbon atoms, or aryl containing 6 to 20 carbon atoms;
$R^2$ is alkyl containing 1 to 9 carbon atoms or aryl containing 6 to 12 carbon atoms;
$R^3$ is alkyl containing 1 to 18 carbon atoms, aryl containing 6 to 20 carbon atoms, or cycloalkyl containing 3 to 12 carbon atoms;
$R^4$ is carboxyaryl containing 7 to 13 carbon atoms, cyano (CN) or amido ($CONH_2$);
$R^5$ and $R^6$ are individually hydrogen, alkyl containing 1 to 18 carbon atoms, or aryl containing 6 to 20 carbon atoms, provided that when one of $R^5$ and $R^6$ is alkyl then both $R^5$ and $R^6$ are alkyl;
n is 1 or 2; and
X is an acid anion.

2. A mesoinoic 1,2,4-triazolium-3-thiolate precursor as in claim 1 wherein $R^4$ is (2-carboxyphenyl structure)

3. 1,4,5-Trimethyl-3-(2-carboxybenzylthio)-1,2,4-triazolium nitrate represented by the formula:

$$\begin{array}{c} \quad\quad\quad\quad\quad\quad NO_3^{\ominus} \\ CH_3-\overset{\oplus}{N}\!\!-\!\!\!-\!\!\!-\!\!N \\ CH_3-C \quad\quad C-S-CH_2-(2\text{-}carboxyphenyl) \\ \diagdown N \diagup \\ | \\ CH_3 \end{array}$$

4. 1,4,5-Trimethyl-3-(cyanomethylthio)-1,2,4-triazolium tetrafluoroborate represented by the formula:

$$\begin{array}{c} CH_3-\overset{\oplus}{N}\!\!-\!\!\!-\!\!\!-\!\!N \quad BF_4^{\ominus} \\ CH_3-C \quad\quad C-SCH_2-CN \\ \diagdown N \diagup \\ | \\ CH_3 \end{array}$$

5. 1,4,5-Trimethyl-3-(carboxamidomethylthio)-1,2,4-triazolium trifluoroacetate represented by the formula:

6. 1,5-Dimethyl-3-(carboxamidomethylthio)-4-amino-1,2,4-triazolium trifluoroacetate represented by the formula:
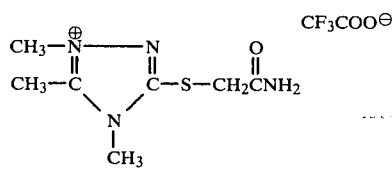
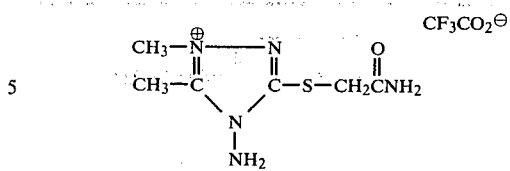
7. A mesoionic 1,2,4-triazolium-3-thiolate precursor represented by the formula:
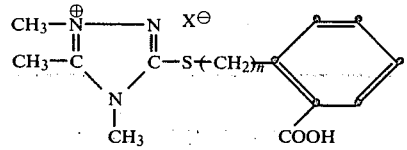
wherein: n is 1 or 2 and X is an acid anion.

UNITED STATES PATENT AND TRADEMARK OFFICE
CERTIFICATE OF CORRECTION

PATENT NO. : 4,404,390
DATED : September 13, 1983
INVENTOR(S) : Henry W. Altland and Daniel D. Shiao It is certified that error appears in the above-identified patent and that said Letters Patent are hereby corrected as shown below:

Column 3, line 64, the part of the structure reading

"$NH_3$" should read -- $NH_2$ --;

Column 4, line 8, the part of the structure reading

"$NH_3$" should read -- $NH_2$ --.

Signed and Sealed this

Seventeenth Day of April 1984

[SEAL]

Attest:

Attesting Officer

GERALD J. MOSSINGHOFF

Commissioner of Patents and Trademarks